United States Patent
Ruch et al.

(10) Patent No.: US 10,835,431 B2
(45) Date of Patent: Nov. 17, 2020

(54) APPARATUS AND METHOD FOR CONTROLLING AN OPERATING TABLE

(71) Applicant: MAQUET GMBH, Rastatt (DE)

(72) Inventors: Juergen Ruch, Offenburg (DE); Matthias Joerger, Achern (DE); Michael Welsch, Gaggenau (DE)

(73) Assignee: MAQUET GMBH, Rastatt (DE)

( * ) Notice: Subject to any disclaimer, the term of this patent is extended or adjusted under 35 U.S.C. 154(b) by 1059 days.

(21) Appl. No.: 14/956,070

(22) Filed: Dec. 1, 2015

(65) Prior Publication Data

US 2016/0095773 A1 Apr. 7, 2016

Related U.S. Application Data

(63) Continuation-in-part of application No. PCT/EP2014/061817, filed on Jun. 6, 2014.

(30) Foreign Application Priority Data

Jun. 6, 2013 (DE) .................. 10 2013 105 869

(51) Int. Cl.
*A61G 7/018* (2006.01)
*G16H 40/63* (2018.01)
(Continued)

(52) U.S. Cl.
CPC .............. *A61G 7/018* (2013.01); *A61G 7/015* (2013.01); *A61G 13/04* (2013.01); *A61G 13/06* (2013.01);
(Continued)

(58) Field of Classification Search
CPC ........ A61G 7/018; A61G 7/015; A61G 13/00; A61G 13/12; A61G 13/08
See application file for complete search history.

(56) References Cited

U.S. PATENT DOCUMENTS 3,754,749 A * 8/1973 Lyon ................ A61G 13/009
5/616
3,868,103 A * 2/1975 Pageot ................ A61G 13/02
137/596

(Continued)

FOREIGN PATENT DOCUMENTS

CN 1140403 A 1/1997
CN 101011311 A 8/2007
(Continued)

OTHER PUBLICATIONS

Communication Pursuant to Article 94(3) EPC for EP14734404.8, dated Mar. 17, 2017, which corresponds to this present application.
(Continued)

*Primary Examiner* — Peter M. Cuomo
*Assistant Examiner* — Ifeolu A Adeboyejo
(74) *Attorney, Agent, or Firm* — Aaron M. Miller

(57) ABSTRACT

An operating table control apparatus is disclosed. The operating table control apparatus has a control device, a plurality of operating table components, and an operating table drive. The plurality of operating table components are actuatable from a first position to a second position via the operating table drive. The second position is a preset position that is stored by the operating table control apparatus. The second position is assigned to a control element of the control device.

26 Claims, 6 Drawing Sheets

(51) Int. Cl.
*A61G 13/06* (2006.01)
*A61G 13/08* (2006.01)
*A61G 13/04* (2006.01)
*A61G 7/015* (2006.01)

(52) U.S. Cl.
CPC ............ *A61G 13/08* (2013.01); *G16H 40/63* (2018.01); *A61G 2200/322* (2013.01); *A61G 2203/12* (2013.01)

(56) References Cited

U.S. PATENT DOCUMENTS

| | | | | |
|---|---|---|---|---|
| 4,501,414 | A * | 2/1985 | Mason | A61G 13/02 378/209 |
| 4,865,303 | A * | 9/1989 | Hall | A61G 13/02 5/614 |
| 4,956,592 | A * | 9/1990 | Schulte | A61G 15/02 318/286 |
| 5,243,267 | A * | 9/1993 | Ogasawara | B60N 2/0232 318/590 |
| 5,467,002 | A * | 11/1995 | Brooks | A61G 15/02 297/330 |
| 5,754,997 | A | 5/1998 | Lussi et al. | |
| 6,000,076 | A * | 12/1999 | Webster | A61G 7/015 5/600 |
| 6,202,230 | B1 * | 3/2001 | Borders | A61G 13/0009 5/613 |
| 6,351,678 | B1 * | 2/2002 | Borders | A61F 7/007 700/83 |
| 6,353,949 | B1 * | 3/2002 | Falbo | A61G 13/04 5/610 |
| 6,752,463 | B2 * | 6/2004 | Nivet | B60N 2/0224 297/330 |
| 6,754,923 | B2 * | 6/2004 | Borders | A61G 12/00 5/618 |
| 7,010,369 | B2 * | 3/2006 | Borders | A47C 31/008 700/90 |
| 7,058,999 | B2 * | 6/2006 | Horitani | A47C 20/041 5/616 |
| 7,089,612 | B2 | 8/2006 | Rocher et al. | |
| 7,246,389 | B2 * | 7/2007 | Taguchi | A61G 7/001 5/608 |
| 7,669,261 | B2 * | 3/2010 | Fruh | A61G 13/02 5/613 |
| 7,694,366 | B2 * | 4/2010 | Koch | A61G 13/04 5/608 |
| 2006/0080777 | A1 * | 4/2006 | Rocher | A61G 13/08 5/618 |
| 2007/0107126 | A1 | 5/2007 | Koch et al. | |
| 2015/0135440 | A1 * | 5/2015 | Chiacchira | A61G 7/015 5/611 |

FOREIGN PATENT DOCUMENTS

| | | |
|---|---|---|
| DE | 4238259 C2 | 6/1995 |
| DE | 19929907 A1 | 12/2000 |
| DE | 19581511 C2 | 5/2001 |
| DE | 19955116 A1 | 5/2001 |
| DE | 102005053754 A1 | 5/2007 |
| DE | 102005054223 A1 | 5/2007 |
| DE | 102005054230 A1 | 5/2007 |
| DE | 102007062200 A1 | 9/2008 |
| EP | 2508160 A2 | 10/2012 |
| JP | 2-185249 A | 7/1990 |
| JP | 2001-522648 A | 11/2001 |
| JP | 2007-130476 A | 5/2007 |
| JP | 2012-130370 A | 7/2012 |
| JP | 2012-228509 A | 11/2012 |
| RU | 2412680 C2 | 2/2011 |

OTHER PUBLICATIONS

Printout of citation—TrumpfMedical video: "Trumpf Medical TruSystem 7000", YouTube: (https://www.youtube.com/watch?v=2pFt_dkOq3A)(XP054977208) video published on May 28, 2013.
English translation of Chinese Office Action and Chinese Search Report dated Nov. 9, 2016 for corresponding Chinese Patent Application No. 201480039954.1, 11 pages.
Japanese Office Action dated Mar. 6, 2018 for corresponding Japanese Patent Application No. 2016-517618, 6 pages (with 6 pages of English translation).
Russian Office Action (with English translation) and Russian Search Report dated Feb. 13, 2018, issued for corresponding Russian Patent Application No. 2015155722, 9 pages.
International Search Report dated Sep. 29, 2014, issued in PCT/EP2014/061817 (with English translation).

* cited by examiner

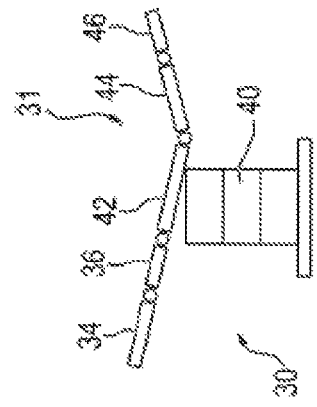
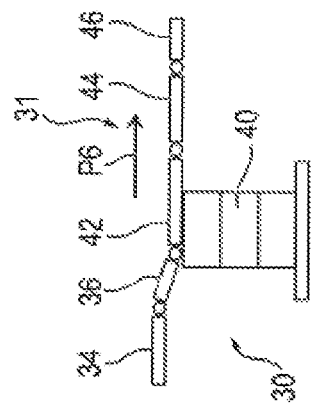
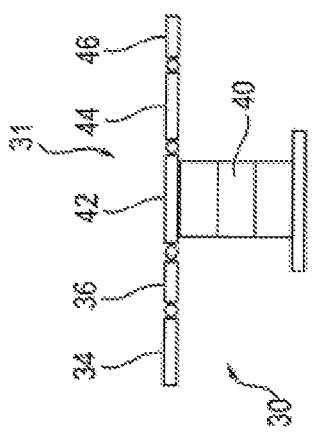
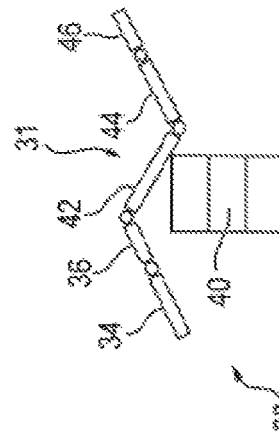
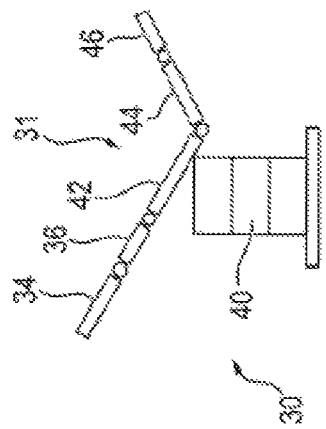

APPARATUS AND METHOD FOR CONTROLLING AN OPERATING TABLE

CROSS REFERENCE TO RELATED APPLICATIONS

The present application is a continuation-in-part filed under 35 U.S.C. § 111(a), and claims the benefit under 35 U.S.C. §§ 365(c) and 371 of PCT International Application No. PCT/EP2014/061817, filed Jun. 6, 2014, and which designates the United States of America, and German Patent Application No. 10 2013 105 869.8, filed Jun. 6, 2013. The disclosures of these applications are herein incorporated by reference in their entirety.

TECHNICAL FIELD

The present disclosure relates to an apparatus and a method for controlling an operating table which may have, e.g., three components, the positions of which are variable by control elements, as well as, e.g., two drive units by which the positions of the second component and of the third component may be variable relative to each other and relative to the first component. Furthermore, the operating table may have a control unit for controlling the drive units wherein in the control unit, at least a first position of the second component and of the third component may be stored relative to each other and relative to the first component.

BACKGROUND

DE 199 55 116 A1 discloses a control unit for controlling the drives of a patient support surface which can be removed from a column for an operating table with electrically adjustable components and which includes an energy supply, a controller and a control unit. The control unit is integrated in a trolley for transporting the lying surface of the operating table.

DE 10 2007 062 200 A1 discloses an operating table with a plurality of components that are adjustable by control elements. The condition and/or the change of state of at least one part of the control elements are/is detected by sensors wherein the signals generated by the sensors are supplied to a processing device.

DE 10 2005 054 230 A1 discloses a method and a system for bi-directional infrared data transmission between an operating table and a control unit. The operating table and the control unit both involve infrared data transmission and both comprise an infrared transmitter and an infrared receiver.

DE 10 2005 054 223 A1 discloses an apparatus for adjusting an operating table, wherein the operating table has a column for an operating table on which an adjustable patient support surface is removably arranged. The apparatus comprises a control unit for entering adjustment commands for adjusting components of the operating table. The adjustment commands can directly be transmitted from the control unit to the adjustable lying surface.

DE 10 2005 053 754 A1 discloses a device for adjusting the patient support surface of an operating table that comprises several segments which can be adjusted relative to each other. At least one portion of the adjustable segments is connected with actuators which are controllable for adjusting the corresponding segments. The input device has a device for entering body-part-related adjustment commands that are associated with the adjustment of the position of a part of the body or portion of the body of a patient lying on a patient support surface.

SUMMARY OF THE DISCLOSURE

With respect to stationary operating tables as well as movable operating tables and mobile operating tables, electrically adjustable components may be provided, such as a column for an operating table and/or a column head for an operating table. The column may be electrically variable in its length in order to change the height of a patient support surface positioned on the column for an operating table. The column head may be adjustable by two orthogonal axes to change the inclination or tilt of the patient support surface connected with the column head of the operating table and/or electrically adjustable components of the patient support surface.

However, with respect to certain operations it may be appropriate to bring a patient again into a position that the patient already had previously been in before during previous operations (e.g., or that other patients had been in before) by a corresponding adjustment of the components of the operating table (e.g., when the setting of this position by one or more control elements has been relatively involved). Furthermore, the components may be adjusted in a manner that is suitable for the patient.

The present disclosure describes an apparatus and a method for controlling an operating table by which a simple and secure setting of components of an operating table in at least one first position of a plurality of components may be possible.

Positions of at least a first component and a second component relative to each other and to a third component may be stored. This position information may be stored as information associating the position of the components to each other and/or the position of drive units.

With respect to the activation of a first control element, the drive units may be controlled in such a way that the components are moved into the stored position. At least one control parameter may be saved as a preset setting wherein the drive units for moving the components may be controlled from at least a second position, which may be different from the stored first position, to the stored first position depending on the stored control parameter. For example, when the components are moved from the second position to the first position, conditions defined by the control parameter may be met so that suitable conditions for a patient lying on a patient support surface formed of at least one part of the components may be maintained while the components are moved from the second position to the first position.

The control parameter may comprise at least one condition to be met when the components are moved. Thus, such a condition can be easily defined and can be met when the components are moved from the second position into the first position or vice versa whereby suitable conditions for a patient lying on a patient support surface formed of at least a portion of the components may be maintained.

The control parameters may comprise permissible degrees of freedom of the movement of the component, permissible angle ranges of position angles of the components to each other, and the possibility of moving the components at the same time. The control parameters may also comprise the possibility of serially moving the components, moving the components in an alternating manner, and sequentially moving the components. The control parameters may further comprise permissible adjustment speeds of the components, permissible profiles of the adjustment speeds of the components, permissible inclinations of the components in a space and/or stored movement sequences between several positions as controllers. The conditions for individual parts of the total movement sequence between two positions may also be defined separately. The control parameter can also limit the movement of individual components, for example the speed of the movement of the component (which may be, for example, a movement parameter). The control parameter for different adjustment positions of the components can be defined differently (for example, by enabling different limiting parameters or by varying control of the drive units. Thus, an individual adjustment of the control parameter for different phases of movement of the adjustment movement of the components may be facilitated.

The first and/or second stored position can be a neutral position of the operating table, a transfer position for the transfer of a patient support surface of the operating table to a trolley, an operation-specific initial position of the components of the operating table and/or an operation-specific operation position. These positions may be selectable by control elements for controlling the operating table, for example by a remote control (for example by a wireless remote control). The positions may be at least partly stored as substantially fixed and unchangeable positions or can be stored as positions defined by a user. Thus, flexible handling and easy manipulation of the operating table for different operations may be facilitated.

A first position and at least a second position may be saved as a preset setting wherein the control unit sets the first position and the second position differently by repeated actuation of the first control element. Alternatively, the control unit can set the first position upon actuating the first control element and the second position upon actuating the second control element via the drive units. Thus, a simplified and intuitive manipulation of the operating table is possible so that a simple change between the first position and the second position (e.g., or any stored further positions) may be possible.

Furthermore, the control unit, when the first control element is deactivated and/or when the second control element is deactivated, may stop the movement of the components even if the first stored position and/or the second position of the components have/has not yet been reached. Thus, the adjustment movement may take place if the control element is actuated so that unsuitable conditions for the patient caused by an improperly controlled or improperly supervised procedure of the components is avoided.

Alternatively or additionally, the sequence of movements can be interrupted if at least one component has been moved into a position which corresponds to the stored position. The movement of the further components into a position which corresponds to the stored position may take place after the control element is subsequently actuated, wherein the actuation of the control element assigned to the position is interrupted at least for a short time.

Any position of the components adjustable by an operator by control elements can be stored as a preset setting. Thus, an operator (e.g., a physician carrying out an operation) can easily store a position of the components that is convenient for him with respect to the operation, so that he or she can subsequently select a position again by actuating the corresponding control element so that the control unit controls the drive units in such a way that the components are again arranged in the stored position.

Furthermore, in the control unit, a second position of the first component relative to the second component and relative to the third component may be stored. The second position may be different from the first stored position, e.g., when an operator changes the position of the components from the first stored position to the second stored position by further control elements, when the control unit stores the sequence of movements caused by this and/or the control information generated by the control unit for controlling the drive units, and/or when the sequence of movements and/or the control information is available for the repeated movement between the two positions by the first control element and/or the second control element.

The stored sequence of movements or the stored control information of the movement of the components from the first position into the second position may be performed inversely relative to a movement of the components from the second position into the first position. Thus, configuring the control parameter by storing the concrete sequence of movements for a movement between the two positions of the control parameter may be facilitated. The movement between the first position and the second position for determining the sequence of movements to be stored may be for example a teach-in drive wherein the movement or the control information of the drive units may be recorded so that it can be used for a later movement of the components between these two positions in both directions (e.g., from the first position to the second position and from the second position to the first position). Thus, simplified handling of the operating table may be possible. This may provide the surgeon with a convenient method to draw on stored positions according to a sequence of movements predetermined by him in a simplified manner. Also, for example, a reversed sequence of movements of the movement of the components may take place when the components are moved from the first stored position into the second stored position (for example, such as when moving the components from the second stored position into the first stored position). Thus, the inverse sequence of movements between the two positions may be facilitated.

Furthermore, the first component and the second component may be components of a patient support surface of the operating table and the third component may be a column for an operating table and/or a column base of an operating table. The components of the patient support surface may include a top plate, a back plate, a central plate, a first one-part or multi-part leg plate and/or a second one-part or multi-part leg plate. The patient support surface may serve the purpose of positioning a patient and can comprise further or alternative components. The first component may be a central plate that is connected with the column head of the operating table and the second component may be a back plate that is connected with the central plate. Alternatively or additionally, the second component can also be a one-part or multi-part leg plate that is connected with the central plate.

Alternatively or additionally, there can also be extension components disposed between the individual components to increase the lying surface provided by the respective components. The third component may be a column for an operating table wherein a base point of the column for the operating table or a point in the column head of the operating table can be used for defining the position of the components relative to the column for the operating table. Alternatively or additionally, a column base of the operating table can be used as a third component wherein a contact surface may also be a column base of the operating table with which the column for the operating table is firmly attached to a construction-side uptake for the inclusion of the column of the operating table. Thus, the detection of the position of the components relative to each other may be facilitated wherein the position of a patient lying on a patient support surface can be easily predetermined via use of the stored positions.

The operating table may have at least one position detection unit. The position detection unit may record the position of the components relative to each other and/or in space. Regarding the detection of a position of components in space, this can be made by specifying the position of the components (e.g., in a global coordinate system). The position detection unit may record the adjustment range, the chronological sequence of the adjustment range, the adjustment speed and/or the chronological sequence of the adjustment speed of a motor serving as a drive unit (e.g., a linear drive serving as a drive unit), and may store the information collected. The position detection unit may have at least one sensor such as, for example, an acceleration sensor, a position sensor, a rotary encoder and/or a pedometer for counting the steps of a stepper motor.

The drive units may comprise at least one stepper motor and the control unit may record the step sequence and/or the chronological sequence of the step sequence of the stepper motor when the control of the components is changed and may store this information. Thus, a simplified recording of the sequence of movements of the component driven by the stepper motor may be provided so that a simple repetition of this sequence of movements is possible.

The control unit may record the duration of the activation of the respective drive unit and/or the speed level activated for this drive unit and may store this information. Based on this stored information, a sequence of movements that has already been executed can easily be reproduced if the same sequence of movements is to be executed.

The components of the operating table may be electrically adjustable by the drive units. The components may comprise, for example, a column for an operating table that is electrically variable in its length for changing the height of a patient support surface positioned on the column for the operating table, a column head of the operating table that is adjustable by two orthogonal axes for changing the inclination and the tilt of the patient support surface connected with the column head of the operating table, and/or electrically adjustable components of the patient support surface.

The first component and the second component can, with respect to the third component, be arranged in a position in which they have been turned by 180° in a horizontal plane and/or in which they are arranged reflected at a vertical plane. Accordingly, if the first component and the second component are parts of the patient support surface and the third component is a column for an operating table, the patient support surface may be arranged on the column for the operating table such that it is turned by 180°. For example, the patient support surface can be connected with the column for the operating table, for example with the column head of the operating table, in two different directions. Alternatively, the first component may be an operating table column, and the second and third components may be arranged relative to the first component.

When connecting the patient support surface with the column for the operating table, the patient support surface can be placed on the column for the operating table by a trolley from two different directions and can be connected with it. In this respect, the first alignment may be a standard alignment and the second alignment may be a reverse alignment.

For example, if the patient support surface is connected with the column for the operating table that is turned by 180°, with respect to the arrangement of the lying surface, is connected with the column for the operating table at the time of the storage of a position of the components, then the position of the first and the second component relative to the third component may be mirrored at a vertical plane (for example, with respect to tilt and inclination of the components or the patient support surface). A stored sequence of movements between two stored positions may be mirrored at this vertical plane as well. The vertical plane may be arranged such that a transverse axis of the patient support surface and/or a transverse axis of the central plate of the patient support surface lie/lies in a neutral position of the patient support surface in this vertical plane. This transverse axis may be orthogonal to its longitudinal axis of the patient support surface or the central plate. Thus, the stored positions as well as the stored sequences of movements between two positions and the stored control parameter, which have been stored in standard alignment of the patient support surface, can also be used in reverse alignment of the patient support surface. Thus, when storing a position and/or a sequence of movements in standard alignment of the patient support surface, it may be accordingly approached in a mirrored way in a reverse alignment of the patient support surface (e.g., the sequence of movements of the movement of the components relative to each other may be mirrored at the vertical plane).

If, for example, one part of the patient support surface is formed by other and/or additional components or if there are external devices that limit the movement of the components of the operating table so that a stored position of the components may not be achieved, a movement of the components may take place (e.g., up to a position which comes closest to the stored position of the components). A stored sequence of movements may be carried out until a limitation of the movement of at least one component has been achieved. For example, a modified structure of the patient support surface or external devices may limit the movement of the components. Then the components may be moved to the position, e.g., that comes closest to the stored position.

Further features and advantages of the present disclosure are described below in conjunction with the exemplary embodiments illustrated in the figures.

BRIEF DESCRIPTION OF THE DRAWINGS

FIG. 1b illustrates an exemplary remote control and operating table according to FIG. 1a after an adjustment of the inclination to tilt starting from the initial position according to FIG. 1a;

FIG. 2 illustrates a schematic side view of the exemplary operating table in a neutral position;

FIG. 3 illustrates the schematic side view of the exemplary operating table in a transfer position;

FIG. 4 illustrates the schematic side view of the exemplary operating table in an initial position with respect to the operation;

FIG. 5 illustrates a schematic side view of the exemplary operating table in a first user-defined position;

FIG. 6 illustrates a schematic side view of the exemplary operating table in a second user-defined position;

DETAILED DESCRIPTION AND INDUSTRIAL APPLICABILITY

Figure 1A:
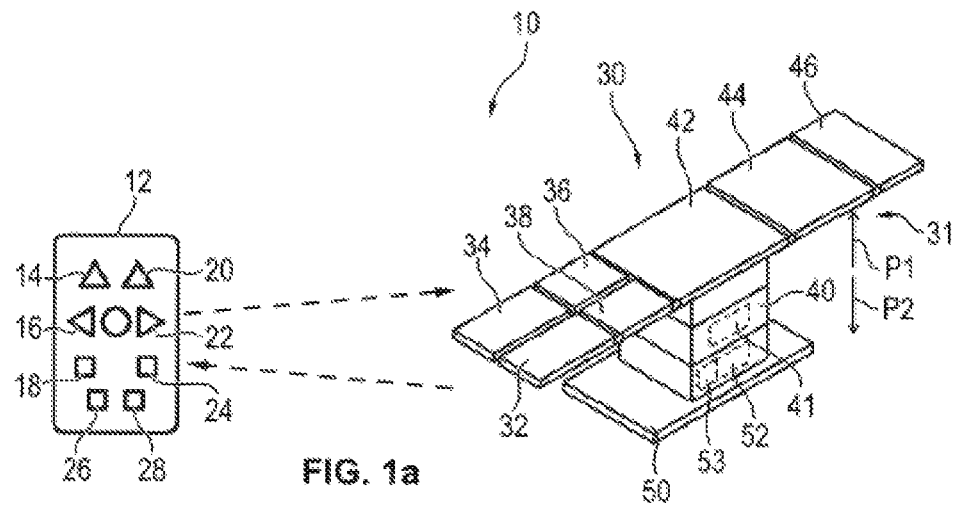
FIG. 1a illustrates an exemplary operating table with several components adjustable by control elements provided by a wireless remote control in an initial position.

FIG. 1a shows an arrangement 10 with a remote control 12 that may have several control elements 14 to 28 (e.g., 14, 16, 18, 20, 22, 24, 26, and 28) by which adjustable components 32 to 46 (e.g., 32, 34, 36, 38, 40, 42, 44, and 46) of an operating table 30 can be adjusted, e.g. can be changed in their position in space and/or with respect to other components 32 to 46. The individual components 32 to 46 or groups of these components 32 to 46 may be assigned to the control elements 14 to 28 of the remote control 12 so that if a control element 14 to 28 is activated, a corresponding adjustment of the component 32 to 46 assigned to this control element 14 to 28 or component group may be carried out by a drive unit that may be provided for this purpose. The drive unit 41 for changing the length of a column 40 for the operating table is shown as an example. The column 40 may be, for example, a substantially vertical operating table column. The drive unit 41 may include, for example, a stepper motor, a hydraulic cylinder, and/or a spindle drive. At the lower end of the column 40 for the operating table, a column base 50 of the operating table may be provided. At the opposite end, the column 40 for the operating table may be connected with a patient support surface 31 that may comprise the components 32 to 36, 42 to 46. Via the drive unit 41, the length of the column 40 for the operating table can be varied and the height of the patient support surface 31 can be changed relative to a floor, e.g. toward the arrows P1 and/or P2 in order to bring a patient who lies on the patient support surface 31 into a position that is suitable for the operation to be performed. The elements of operating table 30 may be controlled via a control unit 52 (e.g., a control device such as a controller), which may include suitable components for controlling the movement and function of the various elements of operating table 30 (e.g., one or more drive units for moving components, sensors, transmitters, and/or receivers). Also for example, control unit 52 may include computer elements suitable for controlling operating table 30. For example, control unit 52 may include a storage device (e.g., a computer-readable medium) for storing information associated with an operation of operating table 30 (e.g., as disclosed herein). Control unit 52 may also include a position detection unit 53 for recording the position of components of operating table 30 relative to each other and/or in space.

Figure 1B:
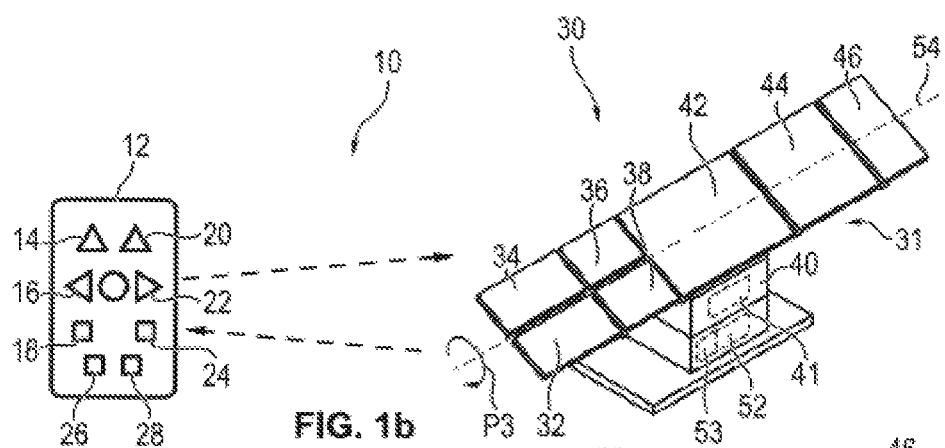
Figure 1C:
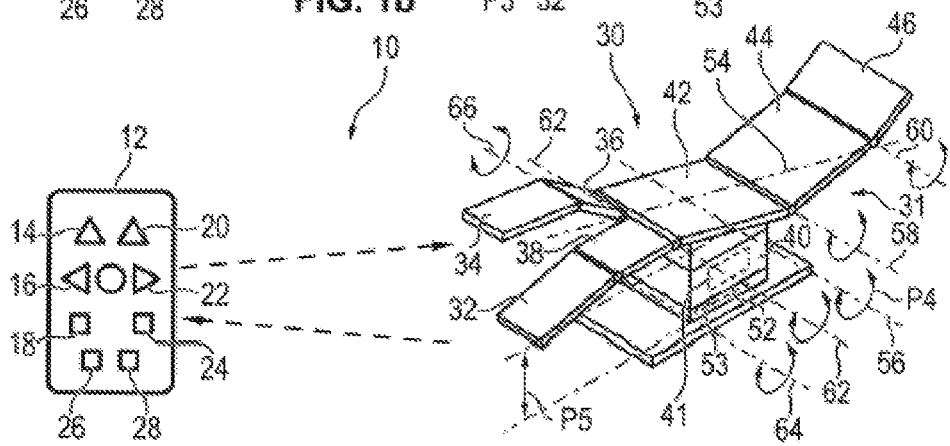
FIG. 1c illustrates the exemplary remote control and operating table according to the FIGS. 1a and 1b in a second adjustment position with respect to the initial position shown in FIG. 1a (e.g., wherein the exemplary patient support surface may be pivoted by an axis of rotation that is orthogonal to its longitudinal axis to the adjustment of the longitudinal inclination and components of the patient support surface may be in addition pivoted by several axes of rotation with respect to the central plate of the patient support surface.

The operating table 30 may comprise further drive units for changing the position of the patient support surface 31, for example, regarding the adjustment of the longitudinal inclination and/or the adjustment of the inclination to tilt with respect to the patient support surface 31 as well as the adjustment of individual components of the patient support surface 31 with respect to further components (e.g., as is shown in FIG. 1c). As illustrated in FIG. 1b, the patient support surface 31 may be turned by its longitudinal axis 54 toward the arrow P3 so that the patient support surface 31 may be laterally tilted. Such a lateral tilting may be, for example, an adjustment of the inclination to tilt (e.g., as a tilt of the patient support surface 31). As can be seen from the central plate 42 of the patient support surface 31 in FIG. 1c, the patient support surface 31, in contrast to FIG. 1a, may be turned by an axis of rotation 56 orthogonally to the longitudinal axis 54 of the patient support surface 31 toward the arrow P4 (e.g., so that a longitudinal inclination of the patient support surface 31 may be adjusted). This adjustment of the longitudinal inclination may be, for example, an inclination of the patient support surface 31. Furthermore, the length of the column 40 for the operating table may be reduced by the drive unit 41 and thus the patient support surface 31 may be lowered toward the arrow P2.

Furthermore, the position of the back plate 44 may be changed by a rotation around the axis of rotation 58 with respect to the central plate 42 and the position of the top plate 46 may be changed by a rotation around the axis of rotation 60 with respect to the back plate 44 of the patient support surface 31. The position of the leg plates comprising the segments 34 and 36 or 32 and 38 may also be changed with respect to the central plate 42 of the patient support surface 31 by a corresponding rotation of the segments 32 to 38 around the axes of rotation 62, 64 and 66. The reduced height of the patient support surface 31 may be illustrated, for example, by the arrow P5 in FIG. 1c.

FIG. 2 shows a schematic side view of the operating table 30 in which the components 32 to 46 may be arranged in a neutral position in which the central plate 42 may be arranged in the middle of the column 40 for the operating table.

FIG. 3 shows a schematic side view of the operating table 30 in which the components 32 to 46 may be arranged in a transfer position in which the components 32 to 38, 42 to 46 of the patient support surface 31 may be arranged higher than in the neutral position due to an extension of a telescope-like (e.g., telescopic) column 40 for the operating table. Also, the components 32 to 38, 42 to 46 of the patient support surface 31 may be moved in the direction of the arrow P6 (e.g., in the direction of the longitudinal axis 54 of the patient support surface 31) into a transfer position for transferring the patient support surface to a trolley for transporting the patient support surface 31 that is separated from the column 40 for the operating table.

FIG. 4 shows a schematic side view of the operating table 30 in which the components 32 to 46 may be arranged in an initial position with respect to an operation, in which the patient support surface 31 has been rotated around the axis of rotation 56 so that the central plate 42 and the leg plates 32 to 38 may be arranged in an inclined position and wherein the back plate 44 with the top plate 46 may be rotated around the axis of rotation 48 with respect to the central plate 42 so that they have an inclination that is opposite to the central plate 42.

FIG. 5 shows a schematic side view of the operating table 30 in which the components 32 to 46 may be arranged in a first user-defined operation position, in which the inclination of the central plate 42 and of the leg plates 32 to 38 may be increased (e.g., in contrast to the initial position with respect to the operation according to FIG. 4). Furthermore, the opposite inclination of the back plate 44 with the top plate 46 may also be increased with respect to the leg plates 32 to 38.

FIG. 6 shows a schematic side view of the operating table 30 in which the components 32 to 46 may be arranged in a second user-defined operation position, in which the leg plates 32 to 38 (e.g., in contrast to the first user-defined position) may be angled with respect to the central plate 42 so that they show the same inclination as the back plate 44 and the top plate 46.

In the present embodiment, the neutral position shown in FIG. 2 may be assigned to the control element 18, the initial position with respect to the operation shown in FIG. 4 may be assigned to the control element 26, the first user-defined operation position shown in FIG. 5 may be assigned to the control element 28, and the second user-defined operation position shown in FIG. 6 may be assigned to the control element 24 of the remote control 12. Thus, the neutral position, the initial position with respect to the operation, the first user-defined position as well as the second user-defined position can easily be set from any position by activating the respective control element 18, 24 to 28. The initial position with respect to the operation, the first user-defined operation position and the second user-defined operation position may be set once via the further control elements 14, 16, 20, 22 of the remote control and may be stored and assigned to the respective control element 18, 24, 26, 28 so that this respective position of the components 32 to 46 can be activated by the control elements 18, 24, 26, 28 and may therefore also be easily adjustable during an operation via remote control 12. In this respect, the movement from any position into the stored position of the components 32 to 46 may be carried out from any position as long as the respective control element 18, 24, 26, 28 is activated. Thus, the movement may be immediately stopped (e.g., or stopped nearly immediately) if the respective control element 18, 24, 26, 28 is no longer actuated (e.g., if the respective control element 18, 24, 26, 28 is released). In case of alternative embodiments, the movement can be continued until an intermediate position or the end position assigned to the respective control element 18, 24, 26, 28, (e.g., the neutral position), the initial position with respect to the operation, the first user-defined operation position or the second user-defined operation position, has been achieved.

Figure 7:
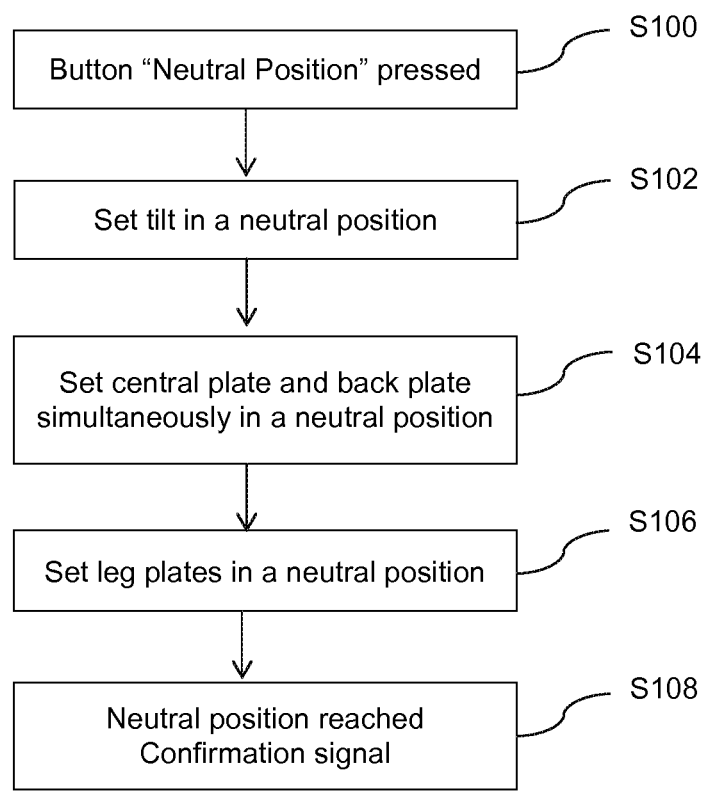
FIG. 7 illustrates a first exemplary flow chart for controlling the movement of the components of the operating table based on an operation position of the components of the exemplary operating table into a neutral position (e.g., of the operating table shown in FIG. 2) with simultaneous movement of the inclination of the central plate and the back plate.

FIG. 7 shows a flow chart regarding the process of the components 32 to 46 of the operating table 30 into the neutral position shown in FIG. 2. The process may be started in step S100 with the control element 18 assigned to the neutral position being actuated by an operator. Subsequently, the tilt of the operating table 30 may be moved into the neutral position in step S102 (e.g. the patient support surface 31 may be rotated around the axis of rotation 54 until it is, with respect to this orthogonal axis of rotation 56, arranged in a horizontal plane).

Subsequently, the inclination of the patient support surface 31 or of the central plate 42 of the patient support surface 31 may be simultaneously rotated around the axis of rotation 56 in step S104 until the longitudinal axis 60 of the patient support surface 31 is also arranged in a substantially horizontal plane. At the same time, the back plate 44 may be changed by the axis of rotation 58 into the neutral position so that subsequently the surfaces of the central plate 42 and of the back plate 44 may be arranged in a substantially horizontal position.

Subsequently (e.g., in step S106), the leg plates 32 to 38 may be rotated around the axes 62, 64, 66 by the respective drives until the surfaces of these leg plates 32 to 38 are also arranged in a substantially horizontal position, (e.g., so that afterwards, the neutral position of the operating table 30, which may be the preset or stored position, may be reached in step S108 and the control unit 52 of the operating table 30 may give a confirmation signal via the remote control 12 or other suitable output).

Figure 8:
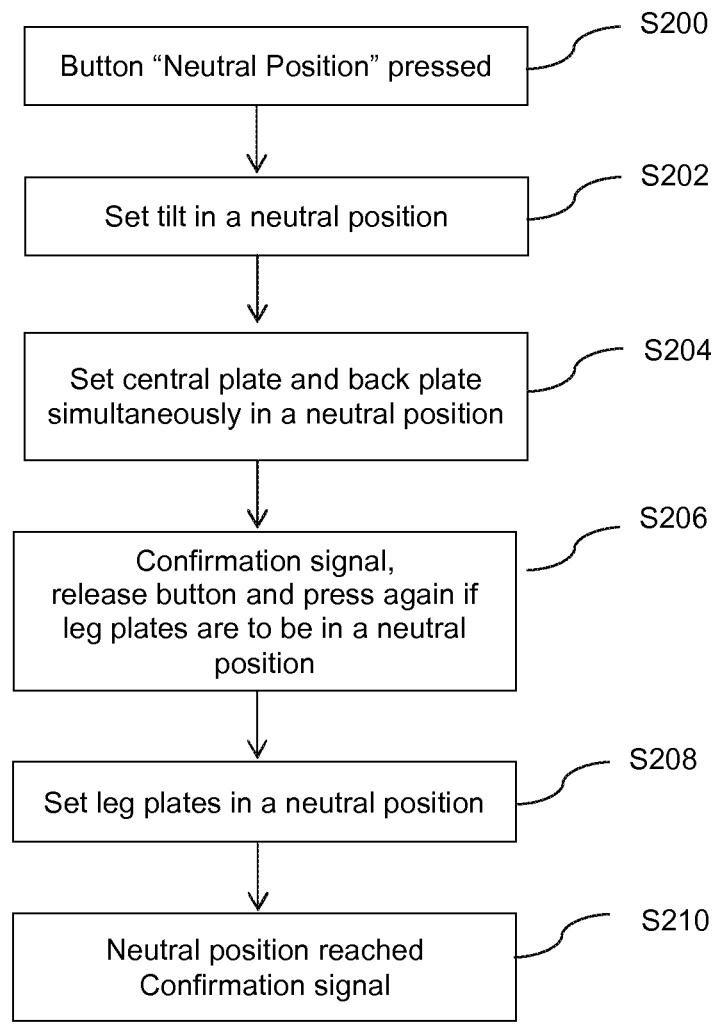
FIG. 8 illustrates a second exemplary flow chart for controlling the movement of the components of the exemplary operating table from an operating table position of the components into a neutral position (e.g., shown in FIG. 2) wherein a stopover is provided.

As an alternative to the procedure shown in FIG. 7, FIG. 8 shows a flow chart of a procedure regarding the movement of the components 32 to 46 of the operating table 30 into the neutral position. The steps S200 to S210 of the procedure according to FIG. 8 may be different from the procedure according to FIG. 7, for example, due to the additional step S206. The steps S200 to S204 generally correspond with the steps S100 to S104 and the steps S208 and S210 generally correspond with the steps S106 and S108. After the simultaneous movement of the central plate 42 and the back plate 44 into the respective neutral positions in step S204, a confirmation signal may be given in step S206 and no further movement of the components 32 to 46 may be activated to further actuate operating table 30 into the neutral position until the control element 18 has been actuated again. For this purpose, the actuating element 18 may not be actuated for a short time and then may be actuated again if the further components (e.g., in the present embodiment the leg plates 32 to 38) are subsequently also to be put in a neutral position. By stopping the movement after having moved the central plate 42 and the back plate 44 into a neutral position, the condition of the patient can again be checked before the movement of the further components 32 to 38 into their neutral positions is activated. The subsequent moving of the leg plates 32 to 38 into their neutral positions in step S208 (which may be a preset or previously stored position) and the subsequent confirmation signal in step S210 may be done in a substantially similar way as has already been described in connection with FIG. 7.

Figure 9:
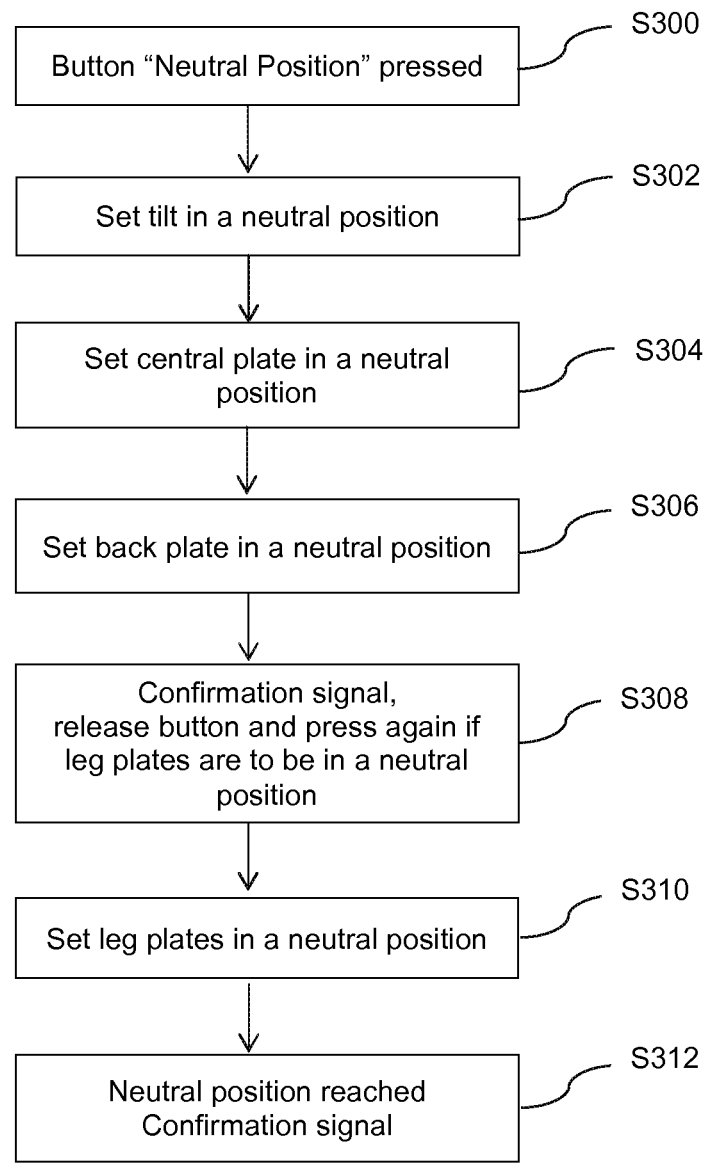
FIG. 9 illustrates an exemplary flow chart for controlling the movements of the components of the exemplary operating table based on an operation position of the components in the neutral position according to FIG. 2 with a stopover and upon successive activation of the adjustment drives of the components.

FIG. 9 shows a flow chart illustrating the procedure of the movement control of the components 32 to 46 of the operating table into the neutral position. The steps S300 and S302 generally correspond with the steps S200 and S202 and the steps S308 to S312 generally correspond with the steps S206 to S210 of the procedure according to FIG. 8. For example, in contrast to the procedure according to FIG. 8, the simultaneous movement of the inclination of the central plate 42 and the back plate 44 in step S204 according to the procedure in FIG. 9 may not take place simultaneously, but may take place successively. For example, at first, the central plate may be moved into the neutral position in step S304 and subsequently, the back plate 44 may be moved into its neutral position in step S306. It is contemplated that any of the positions disclosed herein may be preset or previously stored positions.

Figure 10:
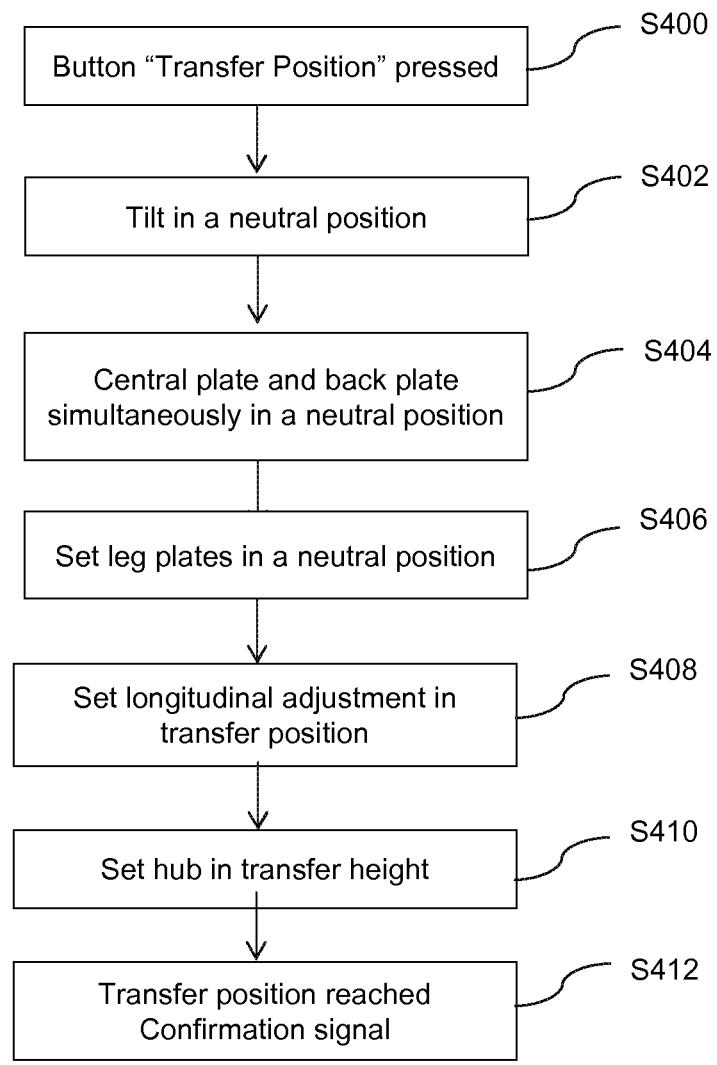
FIG. 10 illustrates a flow chart describing the movement of the components of the exemplary operating table 30 from an operation position to the transfer position shown in FIG. 3.

FIG. 10 shows a flow chart for controlling the movement of the components 32 to 46 into the transfer position shown in FIG. 3. In step S400, the procedure may be started with the activation of the control element 26 of the remote control 12 assigned to the transfer position. Subsequently, the tilt of the central plate 42 may be brought into a neutral position in step S402. Subsequently, the inclination of the central plate 42 and of the back plate 44 may be simultaneously brought into a neutral position in step S404. Subsequently, the leg plates 32 to 38 may be moved into a neutral position in step S406. Subsequently, there may be a longitudinal adjustment of the patient support surface 31 toward the arrow P6 and subsequently, there may be a change of the height of the patient support surface 31 to the transfer position shown in FIG. 3, which may be higher in contrast to the neutral position, by extending the column 40 for the operating table to the respective height via the drive unit 41 of the column 40 for the operating table. After having reached the transfer position in step S412, a confirmation signal may be given by the operating table 30 and/or the remote control 12. In a similar manner as described in connection with the FIGS. 8 and 9, the movement of the further components 32 to 38 can also be stopped with respect to the procedure according to FIG. 10 after having reached a neutral position of a component 42, 44 (e.g., after step S404) until a new input signal is given. Such an interruption of the movement can also be effected with respect to any or all of the procedures shown in the FIGS. 7 to 10 after an intermediate position or an end position of a component 32 to 46 has been reached in order to cause, for example, the operator to control the condition of the patient before any further movement of the components 32 to 46 of the operating table 30.

The first component 42 and the second component 44 can, with respect to the third component 40, also be arranged in a position in which they have been turned by 180° in a horizontal plane and/or in which they are arranged at a vertical plane (e.g., mirrored about a vertical plane) so that if the first component 42 and the second component 44 are parts of the patient support surface 31 of the operating table 30 and the third component is a column 40 for an operating table, the patient support surface 31 may be arranged on the column 40 for the operating table such that it is turned by 180°. In other words, the patient support surface 31 can be connected with the column 40 for the operating table, for example with the column head of the operating table, in two different directions.

When connecting the patient support surface 31 with the column for the operating table 30, the patient support surface 31 can be placed on the column 40 for the operating table by a trolley from two different directions (e.g., in a first alignment and/or in a second alignment) and can be connected with it. In this respect, the first alignment may be a standard alignment and the second alignment may be a reverse alignment.

If the patient support surface 31 that is turned by 180° with respect to the column 40 for the operating table is, with respect to the arrangement of the patient support surface 31, connected with the column 40 for the operating table at the time of the storage of a position of the components 32 to 46, the position of the first and the second component 42, 44 relative to the third component 40 may be mirrored at a vertical plane (for example with respect to tilt and inclination of the components 32 to 38, 42 to 46 or the patient support surface 31). A stored sequence of movements between two stored positions may be mirrored at this vertical plane as well (e.g., two sets of stored sequences of movements that may mirror each other about a vertical plane may be provided). The vertical plane may be for example arranged such that a transverse axis 56 of the patient support surface 31 and/or a transverse axis 56 of the central plate 42 of the patient support surface 31 lie/lies in a neutral position of the patient support surface 31 in this vertical plane. This transverse axis 56 may be orthogonal to the longitudinal axis 54 of the patient support surface or the central plate 42. Thus, the stored positions as well as the stored sequences of movements between two positions and the stored control parameter, which may be stored in standard alignment of the patient support surface 31, can also be used in reverse alignment of the patient support surface 31. Thus, when storing a position and/or a sequence of movements in standard alignment of the patient support surface 31, it may be accordingly approached in a mirrored way in a reverse alignment of the patient support surface 31 (e.g., the sequence of movements of components 32 to 46 relative to each other may be mirrored at the vertical plane). If, for example, one part of the patient support surface 31 is formed by other and/or additional components or if there are external devices that limit the movement of the components 32 to 46 of the operating table 30 so that a stored position of the components 32 to 46 cannot be achieved, a movement of the components 32 to 46 may take place up to a position which comes closest to the stored position of the components 32 to 46. A stored sequence of movements may be carried out until a limitation of the movement of at least one component 32 to 46 has been achieved. For example, a modified structure of the patient support surface 31 or external devices may limit the movement of the components 32 to 46. Then, for example, the components 32 to 46 may be moved to the position that comes closest to the stored position.

It will be apparent to those skilled in the art that various modifications and variations can be made to the disclosed method and apparatus. Other embodiments will be apparent to those skilled in the art from consideration of the specification and practice of the disclosed method and apparatus. It is intended that the specification and the disclosed examples be considered as exemplary only, with a true scope being indicated by the following claims.

What is claimed is:
1. An operating table system, comprising:
a control device;
a plurality of operating table components; and
an operating table drive;
wherein the plurality of operating table components are configured to be actuated from a first position to a second position via the operating table drive;
wherein the second position is a preset position that is stored by the operating table system, and wherein at least some of the plurality of operating table components are positioned differently in the first position than in the second position;
wherein the second position is assigned to a second position control element of the control device;
wherein the control device stores at least one preset control parameter including at least one condition to be met when the plurality of operating table components are moved;
wherein the operating table system is configured to record and store a chronological sequence of movement steps of the plurality of operating table components caused by an operator using control elements to control move- ments of the plurality of operating table components from the first position to the second position; and wherein the operating table system is configured to use the stored chronological sequence of movement steps and the at least one preset control parameter to control future movements of the plurality of operating table components between the first position and the second position, after the operator originally caused movements of the plurality of operating table components from the first position to the second position, by reproducing said chronological sequence of movement steps.

2. The operating table system of claim 1, wherein the plurality of operating table components moves from the first position to the second position when the second position control element is actuated.

3. The operating table system of claim 2, wherein the plurality of operating table components stops moving to the second position when the second position control element is released.

4. The operating table system of claim 1, wherein the second position is a neutral position or a transfer position.

5. The operating table system of claim 1, further comprising:
a position detection unit that records a position of the plurality of operating table components relative to each other and in space;
wherein the position detection unit comprises at least one sensor selected from: an acceleration sensor, a position sensor, a rotary encoder, and a pedometer configured to count steps of a stepper motor.

6. The operating table system of claim 1, wherein:
the operating table drive includes a stepper motor; and
wherein said chronological sequence of movement steps comprises a sequence of steps of the stepper motor and a timing of the sequence of steps of the stepper motor.

7. The operating table system of claim 1 further comprising:
one or more stepper motors, the one or more stepper motors configured to adjust said plurality of operating table components; and
a position detection unit, the position detection unit comprising a pedometer for counting steps of the one or more stepper motors;
wherein the control device is configured to record a chronological step sequence of the one or more stepper motors, and to later reproduce the chronological step sequence using the one or more stepper motors.

8. The operating table system of claim 1:
wherein the control device stores at least one of an activation duration of the operating table drive, and a speed level of the operating table drive, for executing said chronological sequence of movement steps.

9. The operating table system of claim 1, further comprising:
a remote control device;
wherein said plurality of operating table components comprises:
a first operating table component;
a second operating table component that is movable with respect to the first operating table component; and
a third operating table component that is movable with respect to the first operating table component;
wherein the second operating table component and the third operating table component are actuatable from the first position to the second position via the operating table drive.

10. The operating table system of claim 9, wherein:
the first position is a preset position that is stored by the operating table system; and
the first position is assigned to a first position control element of the remote control device.

11. The operating table system of claim 10, wherein, in response to user selection of the first position control element while the plurality of operating table components are in the second position, said stored chronological sequence of movement steps for movement of the plurality of operating table components from the first position to the second position is executed in reverse.

12. The operating table system of claim 9,
wherein the first operating table component comprises a column, wherein the second operating table component comprises a first patient support surface component, and wherein the third operating table component comprises a second patient support surface component;
wherein the first patient support surface component and the second patient support surface component are configured to be rotated 180° with respect to the column; and
wherein, when the first patient support surface component and the second patient support surface component are each rotated 180° with respect to the column and the second position control element is selected, the chronological sequence of movement steps for the first patient support surface component mirrors the chronological sequence of movement steps for the second patient support surface component about a vertical plane.

13. The operating table system of claim 9, wherein:
the first operating table component is a substantially vertical operating table column; and
in the second position, the second operating table component and the third operating table component are in a substantially horizontal position.

14. The operating table system of claim 9, wherein:
the second operating table component is actuated from the first position to the second position via the operating table drive, based on a first actuation of the second position control element by a user;
the operating table control system provides a confirmation signal to the user when the second operating table component reaches the second position; and
subsequently to the confirmation signal being provided, the third operating table component is actuated from the first position to the second position via the operating table drive based on another actuation of the second position control element by the user after the second position control element is not actuated for a period of time after the first actuation of the second position control element by the user.

15. The operating table system of claim 9, wherein at least one of the second operating table component and the third operating table component are tilted about a longitudinal axis and a transverse axis when moving from the first position to the second position to be in a substantially horizontal position in the second position.

16. The operating table system of claim 9, wherein the operating table system provides a confirmation signal to a user when the second operating table component and the third operating table component are in the second position.

17. The operating table system of claim 1, further comprising:
a remote control device;
wherein said plurality of operating table components comprises:

an operating table column;
   a first patient support surface component that is movable with respect to the operating table column;
   a second patient support surface component that is movable with respect to the operating table column; and
   a plurality of third patient support surface components that are movable with respect to the operating table column;
   wherein the first patient support surface component, the second patient support surface component, and the plurality of third patient support surface components are actuatable from the first position to the second position via the operating table drive; and
   wherein the second position control element is part of the remote control device.

18. The operating table system of claim 17,
   wherein the first patient support surface component is a central plate, the second patient support surface component is a back plate, and the plurality of third patient support surface components are leg plates;
   wherein the second position is one of:
      (i) a neutral position in which the central plate, the back plate, and the leg plates are in a substantially horizontal position; and
      (ii) a transfer position in which the central plate and the back plate are in the substantially horizontal position, and the leg plates are in a position that is higher than the substantially horizontal position of the central plate and the back plate.

19. The operating table system of claim 1, further comprising:
   a plurality of operating table drive units configured to move the plurality of operating table components;
   wherein said chronological sequence of movement steps stored by the operating table system comprises control information generated by the control device for controlling the drive units.

20. The operating table system of claim 1:
   wherein the control device is configured to record durations of activation of the operating table drive when the chronological sequence of movement steps is caused by the operator controlling movements of the plurality of operating table components from the first position to the second position;
   wherein said chronological sequence of movement steps stored by the operating table system comprises said durations of activation of the operating table drive caused by the operator using the second position control element; and
   wherein the operating table system is configured to reproduce the recorded durations of activation of the operating table drive.

21. The operating table system of claim 1, wherein the at least one preset control parameter includes each of the following: permissible degrees of freedom of the movement of the plurality of operating table components, permissible angle ranges of position angles of the plurality of operating table components to each other, and a possibility of moving the plurality of operating table components at a same time.

22. The operating table system of claim 1, wherein the at least one preset control parameter includes each of the following: a possibility of serially moving the plurality of operating table components, a possibility of moving the plurality of operating table components in an alternating manner, and a possibility of sequentially moving the plurality of operating table components.

23. The operating table system of claim 1, wherein the at least one preset control parameter includes each of the following: one or more permissible adjustment speeds of the plurality of operating table components, one or more permissible profiles of the adjustment speeds of the plurality of operating table components, one or more permissible inclinations of the plurality of operating table components in a space, and one or more permissible stored movement sequences between the first and second positions of the plurality of operating table components.

24. The operating table system of claim 1, wherein the at least one preset control parameter includes each of the following: one or more separately defined conditions for individual parts of a total movement sequence between the first position and the second position, a limit on the movement of individual components of the plurality of operating table components, and one or more different conditions for different adjustment positions of the plurality of operating table components.

25. An operating table system, comprising:
   a control device;
   a plurality of operating table components; and
   an operating table drive;
   wherein the plurality of operating table components are configured to be actuated from a first position to a second position via the operating table drive;
   wherein the second position is a preset position that is stored by the operating table system, and wherein at least some of the plurality of operating table components are positioned differently in the first position than in the second position;
   wherein the second position is assigned to a second position control element of the control device;
   wherein the control device stores at least one preset control parameter including at least one condition to be met when the plurality of operating table components are moved;
   wherein the operating table system is configured to record and store a chronological sequence of movement steps of the plurality of operating table components caused by an operator using control elements to control movements of the plurality of operating table components from the first position to the second position;
   wherein the operating table system is configured to use the stored chronological sequence of movement steps and the at least one preset control parameter to control future movements of the plurality of operating table components between the first position and the second position, after the operator originally caused movements of the plurality of operating table components from the first position to the second position, by reproducing said chronological sequence of movement steps; and
   wherein the at least one preset control parameter includes at least one of the following: permissible degrees of freedom of the movement of the plurality of operating table components, permissible angle ranges of position angles of the plurality of operating table components to each other, a possibility of moving the plurality of operating table components at a same time, a possibility of serially moving the plurality of operating table components, a possibility of moving the plurality of operating table components in an alternating manner, a possibility of sequentially moving the plurality of operating table components, one or more permissible adjustment speeds of the plurality of operating table components, one or more permissible profiles of the adjustment speeds of the plurality of operating table components, one or more permissible inclinations of the plurality of operating table components in a space, one or more permissible stored movement sequences between the first and second positions of the plurality of operating table components, one or more separately defined conditions for individual parts of a total movement sequence between the first position and the second position, a limit on the movement of individual components of the plurality of operating table components, one or more different conditions for different adjustment positions of the plurality of operating table components, or any combination thereof.

26. An operating table system, comprising:
a control device;
a plurality of operating table components; and
an operating table drive;
wherein the plurality of operating table components are configured to be actuated from a first position to a second position via the operating table drive;
wherein the second position is a preset position that is stored by the operating table system, and wherein at least some of the plurality of operating table components are positioned differently in the first position than in the second position;
wherein the second position is assigned to a second position control element of the control device;
wherein the control device stores at least one preset control parameter including at least one condition to be met when the plurality of operating table components are moved;
wherein the operating table system is configured to record and store a chronological sequence of movement steps of the plurality of operating table components caused by an operator using control elements to control movements of the plurality of operating table components from the first position to the second position;
wherein the operating table system is configured to use the stored chronological sequence of movement steps and the at least one preset control parameter to control future movements of the plurality of operating table components between the first position and the second position, after the operator originally caused movements of the plurality of operating table components from the first position to the second position, by reproducing said chronological sequence of movement steps; and
wherein the at least one preset control parameter includes each of the following: permissible degrees of freedom of the movement of the plurality of operating table components, permissible angle ranges of position angles of the plurality of operating table components to each other, a possibility of moving the plurality of operating table components at a same time, a possibility of serially moving the plurality of operating table components, a possibility of moving the plurality of operating table components in an alternating manner, a possibility of sequentially moving the plurality of operating table components, one or more permissible adjustment speeds of the plurality of operating table components, one or more permissible profiles of the adjustment speeds of the plurality of operating table components, one or more permissible inclinations of the plurality of operating table components in a space, one or more permissible stored movement sequences between the first and second positions of the plurality of operating table components, one or more separately defined conditions for individual parts of a total movement sequence between the first position and the second position, a limit on the movement of individual components of the plurality of operating table components, and one or more different conditions for different adjustment positions of the plurality of operating table components.

* * * * *